US012337161B2

(12) United States Patent
Jadhav et al.

(10) Patent No.: US 12,337,161 B2
(45) Date of Patent: Jun. 24, 2025

(54) PRESSURE-REGULATING CONNECTOR FOR INFUSION

(71) Applicant: CAREFUSION 303, INC., San Diego, CA (US)

(72) Inventors: Amarsinh Deeliprao Jadhav, Bangalore (IN); Muralikrishna Menon, Bangalore (IN); Abin Austin, Thrissur (IN)

(73) Assignee: CareFusion 303, Inc., San Diego, CA (US)

( * ) Notice: Subject to any disclaimer, the term of this patent is extended or adjusted under 35 U.S.C. 154(b) by 549 days.

(21) Appl. No.: 17/715,891

(22) Filed: Apr. 7, 2022

(65) Prior Publication Data

US 2022/0323693 A1    Oct. 13, 2022

Related U.S. Application Data

(60) Provisional application No. 63/173,128, filed on Apr. 9, 2021.

(51) Int. Cl.
*A61M 5/34* (2006.01)
*A61M 5/48* (2006.01)
(Continued)

(52) U.S. Cl.
CPC ............ *A61M 5/345* (2013.01); *A61M 5/488* (2013.01); *A61M 2039/0018* (2013.01);
(Continued)

(58) Field of Classification Search
CPC .................. A61M 5/488; A61M 5/484; A61M 2039/2413; A61M 39/22;
(Continued)

(56) References Cited

U.S. PATENT DOCUMENTS

| 4,863,429 A | 9/1989 | Baldwin |
| 4,986,298 A * | 1/1991 | Martin ..................... A61M 1/74 251/86 |

(Continued)

FOREIGN PATENT DOCUMENTS

EP    2383007 A1    11/2011

OTHER PUBLICATIONS

Queensland Department of Health, "Peripheral intravenous catheter (PIVC) Guideline", Queensland Health, 2012, retrieved from the internet at https://www.health.qld.gov.au/_data/assets/pdf_file/0025/444490/icare-pivc-guideline.pdf.

(Continued)

*Primary Examiner* — Nilay J Shah (57) ABSTRACT

A connector for connecting a container containing a medical fluid to a vascular access device may include an upper housing defining a first internal chamber, and a lower housing coupled to the upper housing and defining a second internal chamber for circulation of the medical fluid into the outlet. The connector may further include a slider disposed at least partially in the first and second internal chambers, and a plug coupled to a distal end of the slider. The slider may be reciprocally movable between (i) an open position, where the plug is spaced apart from a floor of the internal chamber to allow the medical fluid to flow through the outlet, and (ii) a closed position where the plug abuts the floor of the second internal chamber to block the medical fluid from flowing through the outlet.

20 Claims, 6 Drawing Sheets

(51) Int. Cl.
   *A61M 39/00* (2006.01)
   *A61M 39/24* (2006.01)
(52) U.S. Cl.
   CPC ............. *A61M 2039/2413* (2013.01); *A61M 2039/2486* (2013.01); *A61M 2205/3331* (2013.01)
(58) Field of Classification Search
   CPC .. A61M 2039/2486; A61M 2205/3331; A61M 5/345; A61M 5/48; A61M 2205/3351; A61M 2205/3355; F16K 1/306
   See application file for complete search history.

(56) References Cited

U.S. PATENT DOCUMENTS

| | | |
|---|---|---|
| 5,322,511 A | 6/1994 | Armbruster et al. |
| 6,945,954 B2 | 9/2005 | Hochman et al. |
| 8,951,227 B2* | 2/2015 | Nagele ................. A61M 39/24 |
| | | 604/246 |
| 10,269,266 B2 | 4/2019 | Rios et al. |
| 2005/0049556 A1 | 3/2005 | Tanaka |
| 2009/0254049 A1* | 10/2009 | Adams ................. A61M 39/24 |
| | | 604/247 |
| 2014/0194851 A1 | 7/2014 | Burke et al. |
| 2014/0276651 A1* | 9/2014 | Schultz .............. A61M 39/165 |
| | | 53/425 |

OTHER PUBLICATIONS

International Search Report and Written Opinion for Application No. PCT/US2022/020428, dated Jul. 4, 2022, 14 pages.

* cited by examiner

PRESSURE-REGULATING CONNECTOR FOR INFUSION

CROSS-REFERENCE TO RELATED APPLICATIONS

This application claims the benefit of U.S. Provisional Application No. 63/173,128, filed Apr. 9, 2021, the entirety of which is incorporated herein by reference.

TECHNICAL FIELD

The present disclosure generally relates to a connector for connecting a medical container, such as a syringe, to a vascular access device for infusion injection of a medical fluid to a patient, and particularly to pressure-regulating connector for connecting a medical container, such as a syringe, to a vascular access device for infusion injection of a medical fluid at safe infusion pressures.

BACKGROUND

In general, vascular access devices are inserted into veins via peripheral or central vessels. Vascular access devices can be used for infusing fluid (e.g., saline solution, blood, medicaments, and/or total parenteral nutrition) into a patient, withdrawing fluids (e.g., blood) from a patient, and/or monitoring various parameters of the patient's vascular system.

However, vascular access devices can become occluded. To ensure vascular access devices are used properly and do not become occluded, standards of practice have been developed. These standards include a cleaning procedure, which is commonly referred to as a flush procedure. These flush procedures maintain the patency of the vascular access device.

Flush procedures may be enhanced by use of a syringe specifically designed to generate lower injection pressure, such as for instance a 10 mL-diameter syringe barrel, or by use of a "push-pause" or pulsatile flushing technique to remove debris or residue in the catheter that may cause occlusion or other undesirable effects.

However, fast injection of flush fluid into peripheral IV lines leads to transient pressure build-up within the vein where the catheter is sited. This pressure may lead to vein damage (rupture or collapse) and infusate infiltration/extravasation, causing clinical complications and the need to replace the peripheral IV catheter.

The description provided in the background section should not be assumed to be prior art merely because it is mentioned in or associated with the background section. The background section may include information that describes one or more aspects of the subject technology.

SUMMARY

There is therefore a need for a device for delivering a flushing injection pressure that stays below or equal to a predetermined threshold in order to avoid damage to blood vessels.

In accordance with various embodiments of the present disclosure, a connector for connecting a container containing a medical fluid to a vascular access device may include an upper housing having an inlet at a proximal end and an inner surface defining a first internal chamber, and a lower housing coupled to the upper housing, and including an outlet at a distal end, and an inner surface defining a second internal chamber for circulation of the medical fluid into the outlet. The connector may further include a slider disposed at least partially in the first and second internal chamber, and a plug may be coupled to a distal end of the slider. The slider may be reciprocally movable between (i) an open position, where the plug at the distal end of the slider is spaced apart from a floor of the internal chamber to allow the medical fluid to flow through the outlet, and (ii) a closed position where the plug at the distal end of the slider abuts the floor of the second internal chamber to block the medical fluid from flowing through the outlet. The slider may be movable to the open position when the medical fluid applies a fluid pressure less than or equal to a predetermined threshold, and the slider may be movable to the second position when the medical fluid applies a fluid greater than the predetermined threshold.

In accordance with some embodiments, a connector for connecting a container containing a medical fluid to a vascular access device may include an upper housing including an inlet at a proximal end, an outlet at a distal end, and an inner surface defining a first internal chamber, and a lower housing coupled to and fluidly communicated with the upper housing via the outlet. The lower housing may include a proximal end coupled to the distal end of the upper housing, and may define a second internal chamber extending distally from the proximal end. The second internal chamber may terminate in a fluid channel extending through a distal end of the lower housing, and the fluid channel may include an inner surface having a threaded profile extending at least partially along the inner surface The connector may further include a slider disposed at least partially in the first and second internal chambers, and a plug coupled to a distal end of the slider. The slider may be reciprocally movable between (i) an open position, where the plug at the distal end of the slider is spaced apart from a floor of the second internal chamber to allow the medical fluid to flow through the outlet, and (ii) a closed position where the plug at the distal end of the slider abuts the floor of the second internal chamber to block the medical fluid from flowing into the fluid channel and through the outlet. The slider may be movable to the open position when the medical fluid applies a fluid pressure less than or equal to a predetermined threshold, and the slider is movable to the closed position when the medical fluid applies a fluid pressure greater than the predetermined threshold.

In accordance with various embodiments of the present disclosure, a connector for connecting a container containing a medical fluid to a vascular access device may include an upper housing having an inlet at a proximal end and an inner surface defining a first internal chamber, and a lower housing coupled to the upper housing and including an outlet at a distal end, and an inner surface defining a second internal chamber terminating in a fluid channel for circulation of the medical fluid into the outlet. The connector may further include a slider disposed at least partially in the first and second internal chamber, a plug coupled to a distal end of the slider, and an extension member extending longitudinally and distally from the plug into the fluid channel, The slider may be reciprocally movable between (i) an open position, where the plug at the distal end of the slider is spaced apart from a floor of the internal chamber to allow the medical fluid to flow through the outlet, and (ii) a closed position where the plug at the distal end of the slider abuts the floor of the second internal chamber to block the medical fluid from flowing through the outlet. The slider may be movable to the open position when the medical fluid applies a fluid pressure less than or equal to a predetermined threshold, and the slider may be movable to the second position when the medical fluid applies a fluid pressure greater than the predetermined threshold.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The following figures are included to illustrate certain aspects of the embodiments and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Rapid injection of flush fluid into peripheral IV lines leads to transient pressure build-up within the vein where the catheter is situated. This pressure frequently leads to vein damage (rupture or collapse) and infusate infiltration/extravasation, causing clinical complications and the need to replace the catheter.

Flushing is an essential strategy in maintaining patency of a vascular access device. Current flushing methods include employing devices specifically configured to deliver a low infusion pressure (e.g., a 10 milliliter (mL) diameter syringe barrel), and/or to implement a pulsatile flushing technique (also referred to as a push-pause drug infusion). For example, in vitro studies have shown that 10 short boluses of 1 mL interrupted by brief pauses may be more effective at removing solid deposits as compared to continuous low-flow techniques.

Various embodiments of the present disclosure are directed to providing a pressure-regulating connector capable of delivering a fluid at a flushing injection pressure within a predetermined pressure range (e.g., a pressure less than vein rupture pressure, but greater than or equal to generic flushing pressure). Various embodiments of the present disclosure are additionally directed to providing a pressure-regulating connector configured to create flow turbulence in the outlet channel in order to replace the conventional push-pause pulsatile flushing technique.

For example, various embodiments of the present disclosure provide a pressure-regulating mechanism integrated with a needleless valve connector, thereby eliminating the need for additional components, and potentially providing a cost savings. Further, the pressure-regulating connectors and systems of the various embodiments described herein may maintain safe infusion pressure by regulating the flow with a reciprocating slider assembly. Furthermore, the pressure-regulating connectors and systems of the various embodiments described herein include a fluid channel with inner surface having threaded profile, which creates turbulent flow, thereby eliminating the need for the push-pause techniques applied by currently existing connectors.

The slider of the slider assembly may include a head portion and a stem portion. In some embodiments, the head portion may have a disc shape. In some embodiments, the head portion may include a plurality of vanes in the shape or form of a turbine extending radially outwards from the outer surface of the stem portion. For example, in some embodiments, the plurality of vanes may form a Kaplan turbine. The pressure-regulating connector having the plurality of vanes forming a Kaplan turbine as the head portion may provide the further advantage of inducing additional turbulence of the medical fluid flowing into the lumen of the fluid channel (in addition to the turbulence induced by the threaded profile).

In some embodiments, the stem portion may include a plurality of vanes forming a turbine and extending radially outwards from an outer surface of the stem portion. For example, in some embodiments, the plurality of vanes may form a Kaplan turbine on the stem portion. The plurality of vanes may be disposed in the second internal chamber at a position proximal to the plug. The pressure-regulating connector having the plurality of vanes forming a Kaplan turbine on the stem portion may provide the further advantage of inducing additional turbulence of the medical fluid flowing into the lumen of the fluid channel (in addition to the turbulence induced by the threaded profile as discussed above with respect to the pressure-regulating connector).

In some embodiments, the slider may further include an extension member extending longitudinally and distally from the plug into the fluid channel. The extension member may have a plurality of threads protruding radially outwards from an outer surface thereof. The plurality of threads on the extension member may advantageously guide the fluid entering the fluid channel and exiting the outlet into a swirling motion, thereby creating turbulence. Accordingly, the pressure-regulating connector with slider having the plurality of threads disposed in the lumen of the fluid channel may provide the further advantage of inducing additional turbulence of the medical fluid flowing into the fluid channel (in addition to the turbulence induced by the threaded profile of the fluid channel as discussed above).

Figure 1:
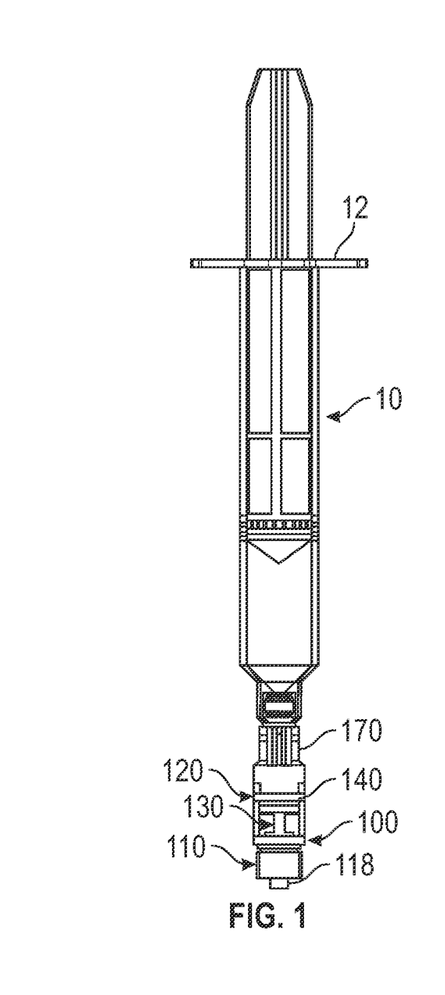
FIG. 1 illustrates an isometric view of a pressure-regulating connector coupled to a syringe, in accordance with some embodiments of the present disclosure.
Figure 2A:
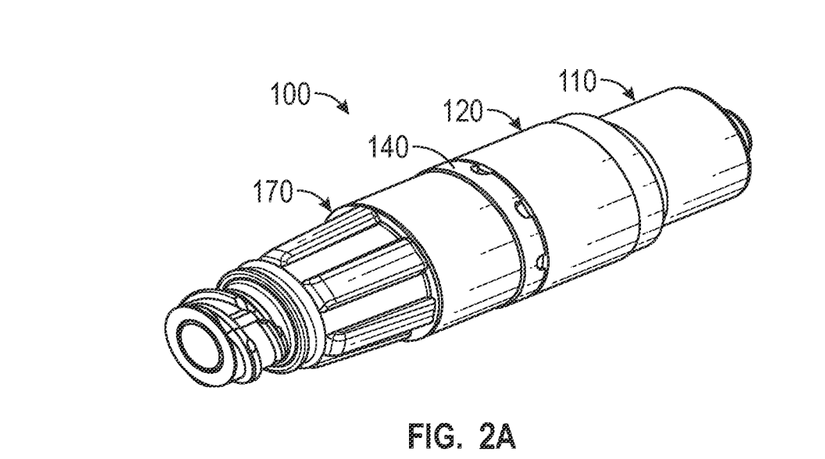
FIG. 2A illustrates a perspective view of the pressure-regulating connector, in accordance with some embodiments of the present disclosure.
Figure 2B:
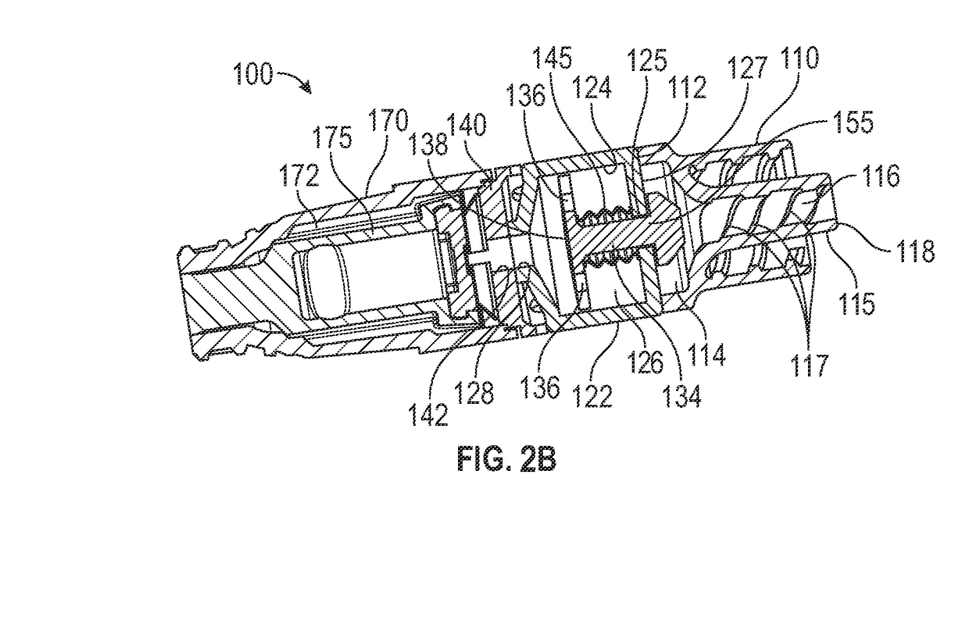
FIG. 2B illustrates a cross-sectional view of the pressure-regulating connector of FIG. 2A, in accordance with some embodiments of the present disclosure.
Figure 3A:
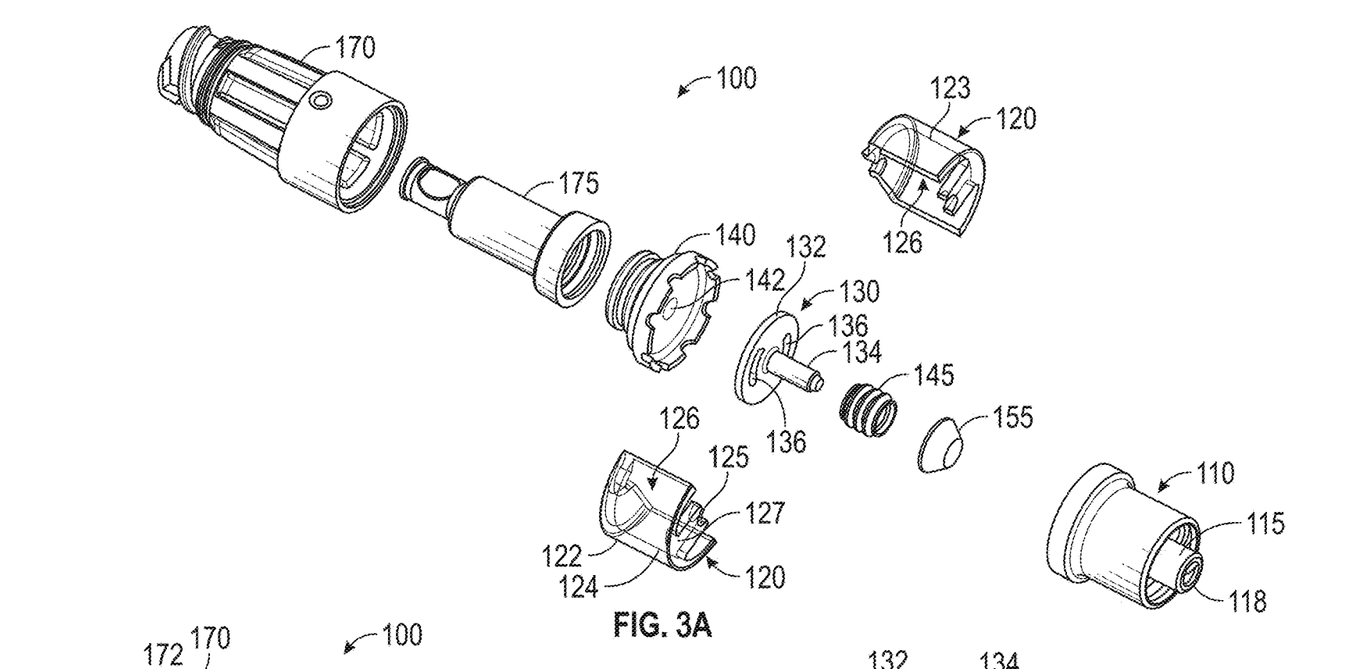
FIG. 3A illustrates an exploded perspective view of the pressure-regulating connector of FIG. 2A, in accordance with some embodiments of the present disclosure.
Figure 3B:
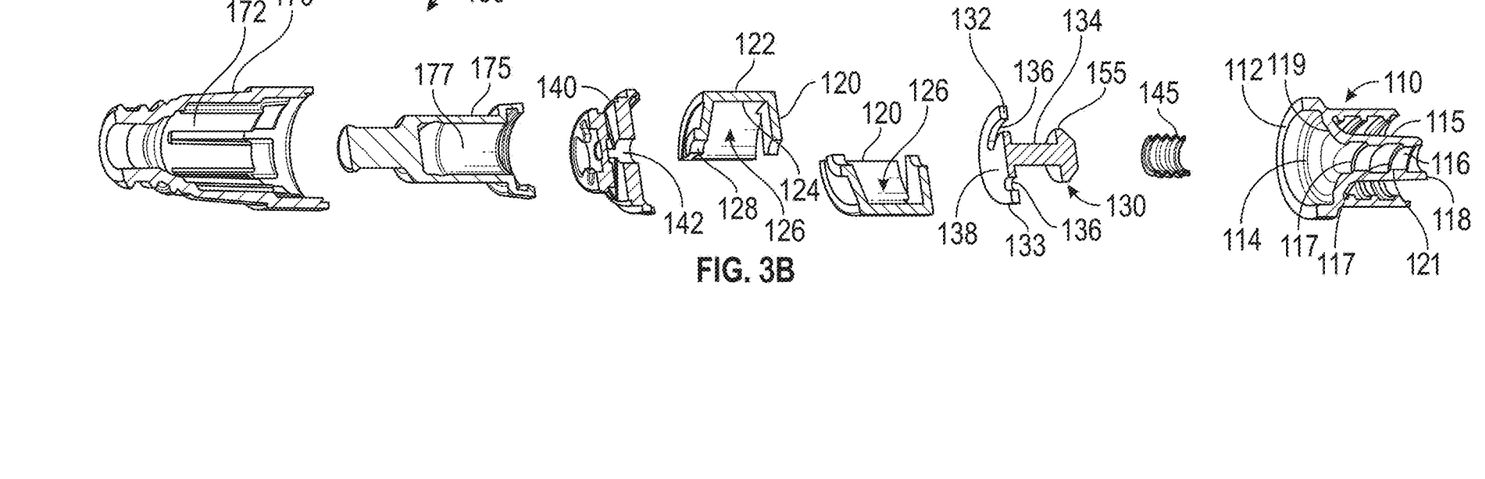
FIG. 3B illustrates an exploded cross-sectional view of the pressure-regulating connector of FIG. 2A, in accordance with some embodiments of the present disclosure.

FIG. 1 illustrates an isometric view of a pressure-regulating connector 100 coupled to a syringe 10, in accordance with some embodiments of the present disclosure. FIG. 2A illustrates a perspective view of the pressure-regulating connector, in accordance with some embodiments of the present disclosure. FIG. 2B illustrates a cross-sectional view of the pressure-regulating connector 100 of FIG. 2A, in accordance with some embodiments of the present disclosure. FIG. 3A illustrates an exploded perspective view of the pressure-regulating connector 100 of FIG. 2A, in accordance with some embodiments of the present disclosure. FIG. 3B illustrates an exploded cross-sectional view of the pressure-regulating connector 100 of FIG. 2A, in accordance with some embodiments of the present disclosure.

As depicted in FIG. 1, in some embodiments, the pressure-regulating connector 100 may be configured to connect a medical container 10, such as a prefilled or pre-fillable syringe, to a vascular access device, such as an IV (intravenous) catheter, such that the medical fluid contained in the syringe 10 passes through the pressure-regulating connector 100 before reaching the vascular access device. Referring to FIGS. 1-3B, the pressure-regulating connector 100 may include an upper housing 120 having an inlet 128 at a proximal end, an outlet 125 at a distal end, and an inner surface 124 defining a first internal chamber 126. The pressure-regulating connector 100 may further include a lower housing 110 coupled to and fluidly communicated with the upper housing 120 via the upper housing outlet 125. The lower housing 110 may include a proximal end 112 coupled to the distal end of the upper housing 120, and may define a second internal chamber 114 extending distally from the proximal end 112. As depicted, the second internal chamber 114 may terminate in a fluid channel 115 extending through a distal end of the lower housing 110. Accordingly, a distal end of the fluid channel 115 may define the outlet 118 of the lower housing 110. The fluid channel 115 may include an inner surface 121 defining a lumen 116 of the fluid channel 115. In some embodiments, the inner surface 121 may have a threaded profile 117 extending at least partially along the inner surface 121. For example, in some embodiments, the threaded profile 117 may include a plurality of helical threads spaced apart from each other. In other embodiments, the threaded profile 117 may include a plurality of circular threads spaced apart from each other. In operation, as the fluid flows through the portion of the lumen 116 having the threaded profile, the threaded profile 117 may cause the fluid to swirl around and create turbulence in the fluid exiting the pressure-regulating connector 100.

The pressure regulating connector 100 including the fluid channel 115 with inner surface having a threaded profile 117 may be advantageous over currently existing connectors in that the turbulence caused as the medical fluid travels through the portion of the fluid channel 115 having the threaded profile 117 reduces or otherwise eliminates the need for a separate push-pause mechanism as implemented in currently existing connectors.

In some embodiments, the pressure-regulating connector 100 may further include a slider 130 disposed and supported at least partially in the first and second internal chambers 126 and 114, and a plug 155 coupled to a distal end of the slider 130. In some embodiments, the plug 155 may be in the form of a rubber plug or stopper. However the various embodiments of the present disclosure are not limited to the aforementioned configuration. As shall be described with further reference to FIGS. 4A-6B, the slider 130 may be reciprocally movable between (i) an open position (illustrated in FIGS. 5A and 5B) where the plug 155 at the distal end of the slider 130 is spaced apart from a floor 119 of the second internal chamber 114 to allow the medical fluid to flow through the outlet port 118, and (ii) a closed position (illustrated in FIGS. 6A and 6B) where the plug 155 at the distal end of the slider 130 abuts a floor 119 of the second internal chamber 114 to block the medical fluid from flowing into the fluid channel 115 and through the outlet 118 of the lower housing 110. The slider 130 may be movable to the first position when the medical fluid applies a fluid pressure less than or equal to a predetermined threshold, and the slider 130 may be movable to the second position when the medical fluid applies a fluid pressure greater than the predetermined threshold. In some embodiments, the predetermined threshold may be 25 pounds per square inch (psi).

In some embodiments, the pressure-regulating connector 100 may include a resilient member 145 mounted in the first internal chamber 126 surrounding at least a portion of the slider 130. The resilient member 145 may exert a proximal force on the slider 130 such that the resilient member 145 maintains the slider 130 away from the closed position as long as the pressure applied by the medical fluid is lower than or equal to the predetermined threshold. The resilient member 145 may be in the form of a bellows extending around an outer surface of the slider 130. For example, in some embodiments, the resilient member 145 may be in the form of a rubber bellows. However, the various embodiments of the present disclosure are not limited to the aforementioned configuration. In some embodiments, the resilient member 145 may be any elastic or other spring material capable of compressing when subject to an axial force, and expanding upon release or reduction of the axial force. In some embodiments, the resilient member 145 may extend around an outer surface of the stem portion 134 of the slider 130.

As depicted, the slider 130 may include a head portion 132 and a stem portion 134 extending distally from the head portion 132. When the medical fluid applies the pressure greater than the predetermined threshold to the head portion 132, the resilient member 145 may compress to allow the slider 130 to move distally to the closed position where the plug 155 blocks the medical fluid from flowing into the fluid channel 115 and out through the outlet 118. In some embodiments, the head portion 132 of the slider 130 may have a disc shape. As depicted, the stem portion 134 of the slider 130 may be in the form of an elongate rod connecting the head portion 132 to the plug 155.

In accordance with some embodiments, the head portion 132 of the slider 130 may include a peripheral edge 133 configured to guide sliding motion of the slider 130 between the open and closed positions. The head portion 132 may further include least one aperture 136 extending distally through the head portion 132 through which the medical fluid flows from the first chamber 126 into the second chamber 114. In some embodiments, the at least one aperture 136 may be a plurality of apertures 136 which may be symmetrically disposed about a central longitudinal axis of the slider 130. As depicted, the plurality of apertures 136 may be two apertures. However, the various embodiments of the present disclosure are not limited to the aforementioned configuration, and the plurality of apertures 136 may include more than two apertures. The plurality of apertures 136 may allow the medical fluid to pass through the head portion 132 and into the fluid channel 115 via the second internal chamber 114. As illustrated, the apertures 136 may be symmetrically disposed, with respect to a longitudinal plane including the central longitudinal axis of the slider 130, so that the flow of the medical fluid may remain symmetric. However, the various embodiments of the present disclosure are not limited to the aforementioned configuration. In some embodiments, the peripheral edge 133 of the head portion 132 of the slider 130 may include notches allowing the medical fluid to pass by the slider 130.

According to various embodiments of the present disclosure, the pressure-regulating connector 100 may further include a needleless connector 170 mounted to the upper housing 120 and fluidly coupled to the slider 130. As depicted, the needleless connector 170 may include a base plate 140 defining an outlet 142 of the needleless connector 170. The outlet 142 of the needleless connector 170 and the inlet 128 of the upper housing 120 may fluidly communicate a fluid chamber 172 of the needleless connector 170 with the head portion 132 of the slider 130 such that the fluid pressure may be exerted on the head portion 132.

Figures 4A, 4B, 5A, 5B, 6A, 6B:
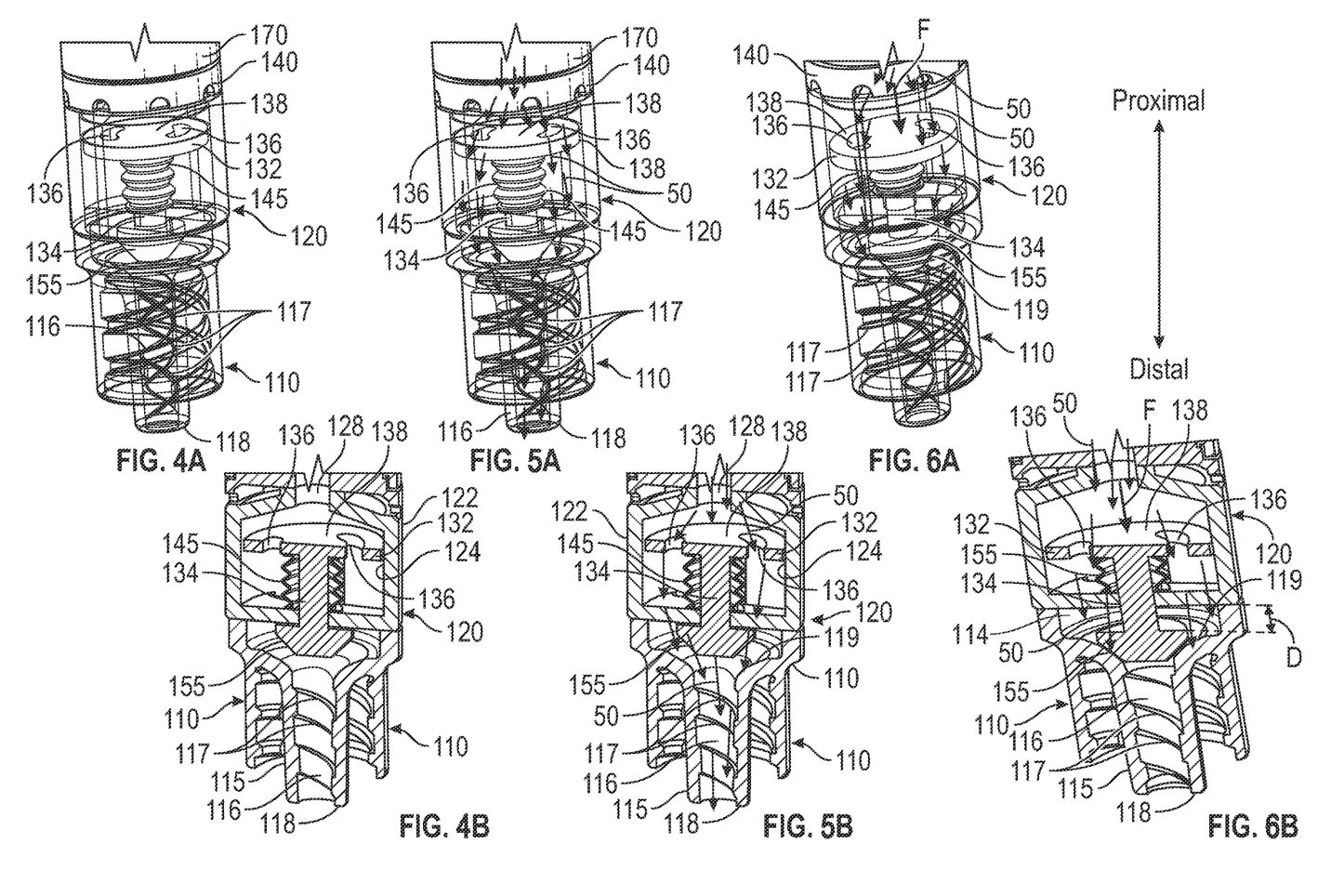
FIG. 4A illustrates a partial perspective view of the pressure-regulating connector prior to operation, in accordance with some embodiments of the present disclosure.
FIG. 4B illustrates a partial cross-sectional view of the pressure-regulating connector prior to operation, in accordance with some embodiments of the present disclosure.
FIG. 5A illustrates a partial perspective view of the pressure-regulating connector during operation in the open position, in accordance with some embodiments of the present disclosure.
FIG. 5B illustrates a partial cross-sectional view of the pressure-regulating connector during operation in the open position, in accordance with some embodiments of the present disclosure.
FIG. 6A illustrates a partial perspective view of the pressure-regulating connector during operation in the closed position, in accordance with some embodiments of the present disclosure.
FIG. 6B illustrates a partial cross-sectional view of the pressure-regulating connector during operation in the closed position, in accordance with some embodiments of the present disclosure.

FIG. 4A illustrates a partial perspective view of the pressure-regulating connector prior to operation, in accordance with some embodiments of the present disclosure. FIG. 4B illustrates a partial cross-sectional view of the pressure-regulating connector prior to operation, in accordance with some embodiments of the present disclosure. As illustrated in FIGS. 4A and 4B, in the absence of a medical fluid circulating inside the pressure-regulating connector 100, the resilient member 145 maintains the slider 130 in a position corresponding to the proximal-most position of the slider 130.

FIG. 5A illustrates a partial perspective view of the pressure-regulating connector 100 during operation in the open position, in accordance with some embodiments of the present disclosure. FIG. 5B illustrates a partial cross-sectional view of the pressure-regulating connector 100 during operation in the open position, in accordance with some embodiments of the present disclosure. When the user pushes the plunger 12 of the medical container (e.g., syringe 10) for infusing the medical fluid, fluid pressure gets built within the syringe 10. Accordingly, a distal pressure is exerted on a top surface 138 of the head portion 132 of slider 130. This distal pressure may displace or otherwise move the slider 130 distally, thereby compressing the resilient member 145. As long as the fluid pressure is less than or equal to the predetermined threshold, the slider 130 may be maintained by the resilient member 145 in the open position (FIGS. 5A and 5B). In some embodiments, the predetermined pressure threshold corresponds to what is considered safe infusion pressure. For example, the predetermined threshold pressure may be equal to approximately 25 pounds per square inch (psi). As previously described, and as illustrated in FIGS. 5A and 5B, in the open position, the plug 155 at the distal end of the slider 130 may be spaced apart from a floor 119 of the second internal chamber 114 to allow the medical fluid to flow through the outlet 118.

FIG. 6A illustrates a partial perspective view of the pressure-regulating connector 100 during operation in the closed position, in accordance with some embodiments of the present disclosure. FIG. 6B illustrates a partial cross-sectional view of the pressure-regulating connector 100 during operation in the closed position, in accordance with some embodiments of the present disclosure. As depicted in FIGS. 6A and 6B, when the fluid pressure is greater than or exceeds the predetermined threshold for what is considered safe infusion, the distal force exerted on the slider 130 may cause the slider 130 to be further displaced or otherwise moved distally a distance D along the length of the fluid channel 152 towards the closed position, illustrated for example in FIGS. 6A and 6B. For example, the resilient member 145 may further compress to allow the slider 130 to be displaced a second distance to the closed position when the medical fluid applies the fluid pressure that is greater than the predetermined threshold for safe infusion. In some embodiments, when the fluid pressure is greater than safe infusion pressure (for example, 25 psi), the slider 130 may travel further distally by further compressing the resilient member 145.

The slider 130 may continue to be displaced further distally by the fluid pressure until the plug 155 abuts against the floor 119 of the second internal chamber 114. Accordingly, the slider 130 may be prevented from moving further distally past the second or closed position, as illustrated in FIGS. 6A and 6B. When the total slider movement or displacement D is equal to approximately 2 millimeters (mm), the plug 155 at the distal end of the slider 130 blocks the fluid from flowing into the fluid channel 152. As previously discussed, in the closed position, the plug 155 at the distal end of the slider 130 may abut the floor 119 of the second internal chamber 114 to block the medical fluid from flowing through the outlet 118. Accordingly, medical fluid having fluid pressure equal to or greater than the threshold safe amount may be trapped inside the first and/or second internal chambers 126 and 114 and cannot flow into the vascular access device. As such, infusion pressure of the medical fluid to the vascular access device may be maintained at or below safe infusion pressures, thereby advantageously preventing issues commonly occurring with currently existing infusion connectors.

For example, an issue commonly associated with infusion procedures is that rapid injection of flush fluid into peripheral IV lines leads to transient pressure build-up within the patient's vein where the catheter is inserted. This pressure frequently leads to vein damage (rupture or collapse) and infusate infiltration/extravasation, causing complications and the need to replace the PIV catheter. Since the pressure-regulating connector of the various embodiments described herein maintains the infusion pressure of the medical fluid to the vascular access device at or below safe infusion pressures, the aforementioned issues commonly occurring with currently existing infusion connectors are minimized or altogether eliminated. The pressure-regulating connector of the various embodiments described herein is advantageously capable of delivering flushing injection pressure within a predetermined pressure range that is less than vein rupture pressure.

When the fluid pressure decreases to a point where it is lower than the predetermined threshold again, the resilient member 145 may push the slider 130 proximally towards the open position of at least FIGS. 5A and 5B. The plug 155 at the distal end of the slider 130 may move proximally away from the floor 119 of the second internal chamber 114, thereby creating a gap or space between the plug 155 and the lumen 116 of the fluid channel 115, and allowing the medical fluid to again enter the fluid channel 115 via the second internal chamber 114. Accordingly, the medical fluid may then flow through the fluid channel 115, exit the pressure-regulating connector 100, and circulate into the vascular access device.

Figure 7A:
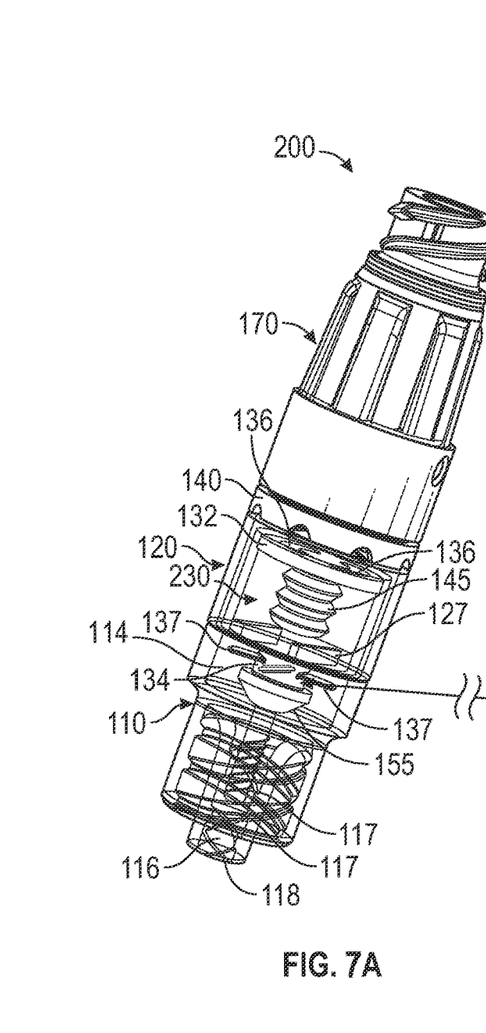
FIG. 7A illustrates a perspective view of a pressure-regulating connector, in accordance with some embodiments of the present disclosure.
Figure 7B:
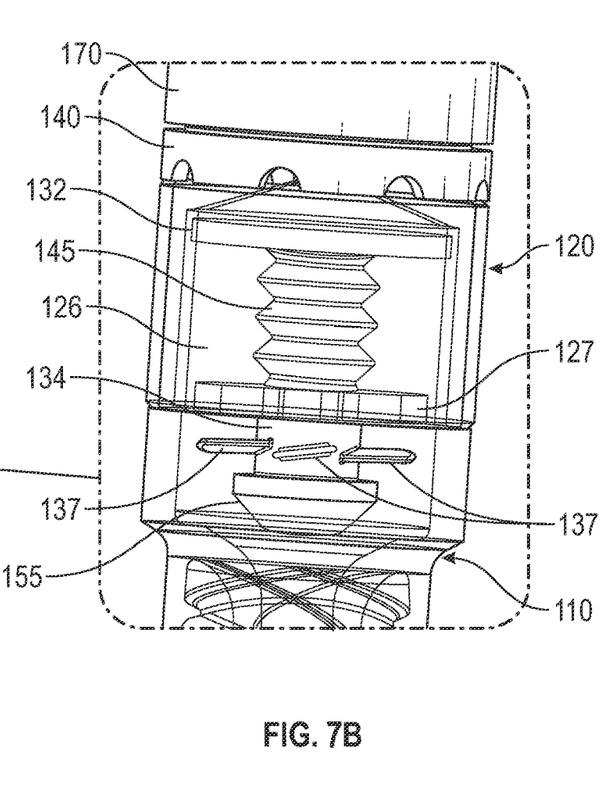
FIG. 7B illustrates a partially enlarged view of the pressure-regulating connector of FIG. 7A, in accordance with some embodiments of the present disclosure.
Figure 7C:
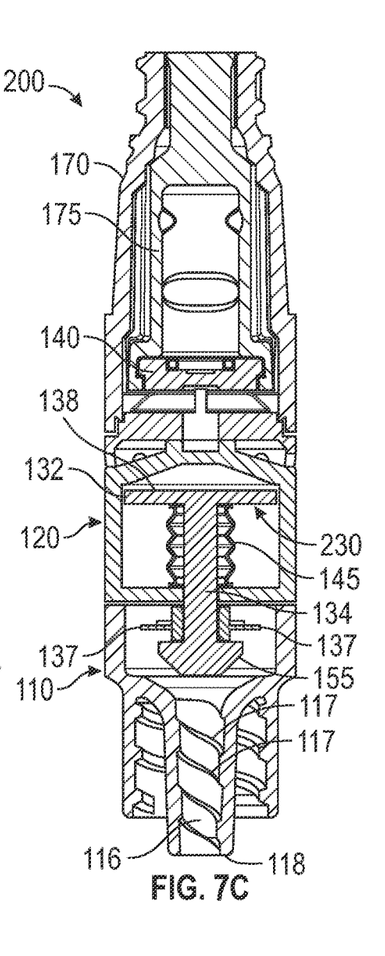
FIG. 7C illustrates a cross-sectional view of the pressure-regulating connector of FIG. 7A, in accordance with some embodiments of the present disclosure.

FIG. 7A illustrates a perspective view of a pressure-regulating connector 200, in accordance with some embodiments of the present disclosure. FIG. 7B illustrates a partially enlarged view of the pressure-regulating connector 200 of FIG. 7A, in accordance with some embodiments of the present disclosure. FIG. 7C illustrates a cross-sectional view of the pressure-regulating connector 200 of FIG. 7A, in accordance with some embodiments of the present disclosure. Similar to the pressure-regulating connector 100, the pressure-regulating connector 200 may include an upper housing 120 including a first internal chamber 126, a lower housing 110 including a second internal chamber 114, a slider 230 disposed and supported at least partially in the first and second internal chambers 126 and 114, and a plug 155 coupled to a distal end of the slider 230. As depicted, the slider 230 may be reciprocally movable between (i) an open position (illustrated in FIGS. 4A and 4B) where the plug 155 at the distal end of the slider 230 is spaced apart from the floor 119 of the second internal chamber 114 to allow the medical fluid to flow through the outlet port, and (ii) a closed position where the plug at the distal end of the slider 230 abuts the floor 119 of the second internal chamber to block the medical fluid from flowing into the fluid channel 115 and through the outlet 118 of the lower housing 110. The slider 230 may be movable to the first or open position when the medical fluid applies a fluid pressure less than or equal to the predetermined threshold, and the slider 230 may be movable to the second position when the medical fluid applies a fluid pressure greater than the predetermined threshold.

In some embodiments, the pressure-regulating connector 200 may include a resilient member 145 mounted in the first internal chamber 126 surrounding at least a portion of the slider 230 to exert a proximal force on the slider 230 such that the resilient member 145 maintains the slider 230 away from the closed position as long as the pressure applied by the medical fluid is lower than or equal to the predetermined threshold. The resilient member 145 may be in the form of a bellows extending around an outer surface of the slider 230. For example, in some embodiments, the resilient member 145 may extend around an outer surface of the stem portion 134 of the slider 230.

As depicted, the slider 230 may include a head portion 132 and a stem portion 134 extending distally from the head portion 132. When the medical fluid applies the pressure greater than the predetermined threshold to the head portion 132, the resilient member 145 may compress to allow the slider 230 to move distally to the closed position where the plug 155 blocks the medical fluid from flowing through the outlet 118. In some embodiments, the predetermined threshold may be 25 pounds per square inch (psi).

In some embodiments, similar to the pressure-regulating connector 100, the head portion 132 of the slider 230 may have a disc shape. For example, in some embodiments, the top surface 138 of the head portion 132 may have a circular shape having a surface area ranging from about 30 mm$^2$ to 35 mm$^2$, in some instances ranging from about 31 mm$^2$ to 34 mm$^2$, more typically from about 32.5 mm$^2$ to 33.5 mm$^2$, and in some embodiments approximately 33 mm$^2$. Though recited in terms of certain ranges, it will be understood that all ranges from the lowest of the lower limits to the highest of the upper limits are included, including all intermediate ranges or specific angles, within this full range or any specifically recited range.

As depicted, the stem portion 134 of the slider 2230 may be in the form of an elongate rod connecting the head portion 132 to the plug 155. In some embodiments, the stem portion 134 may further include a plurality of vanes 137 forming a turbine and extending radially outwards from an outer surface of the elongate rod of stem portion 134. For example, in some embodiments, the plurality of vanes 137 may form a Kaplan turbine on the stem portion 134. As depicted, the plurality of vanes 137 may be disposed in the second internal chamber 114 at a position proximal to the plug 155. The operation of the pressure-regulating connector 200 may be similar to that described with respect to the pressure-regulating connector. However, in addition, the pressure-regulating connector 200 having the plurality of vanes 137 forming a Kaplan turbine on the stem portion 134 may provide the further advantage of inducing additional turbulence of the medical fluid flowing into the lumen 116 of the fluid channel 115 (in addition to the turbulence induced by the threaded profile 117 as discussed above with respect to the pressure-regulating connector 100).

Figure 8A:
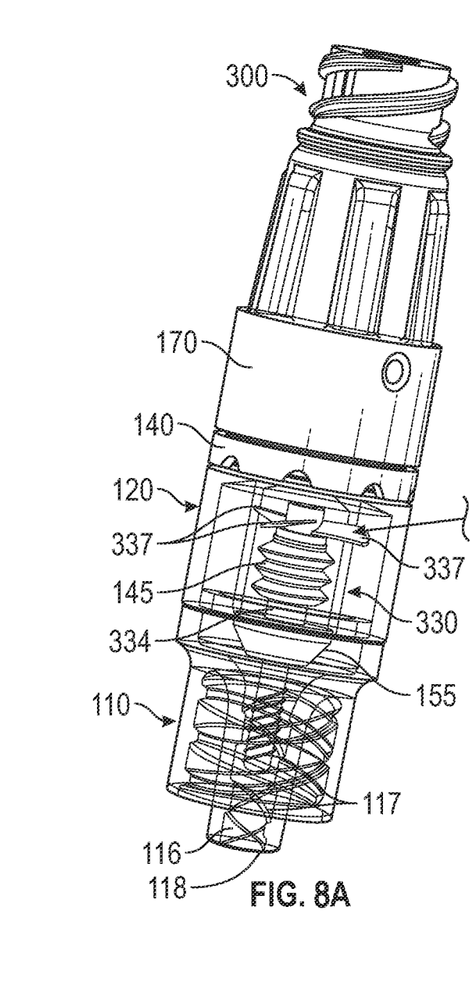
FIG. 8A illustrates a perspective view of a pressure-regulating connector, in accordance with some embodiments of the present disclosure.
Figure 8B:
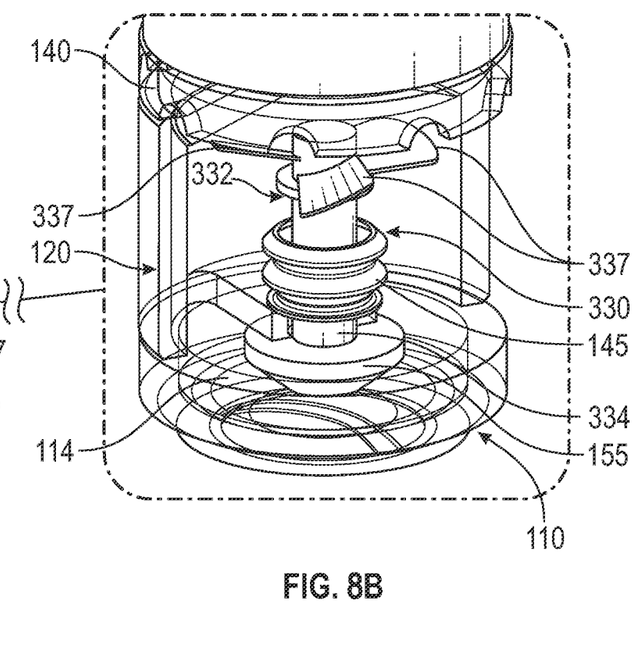
FIG. 8B illustrates a partially enlarged view of the pressure-regulating connector of FIG. 8A, in accordance with some embodiments of the present disclosure.
Figure 8C:
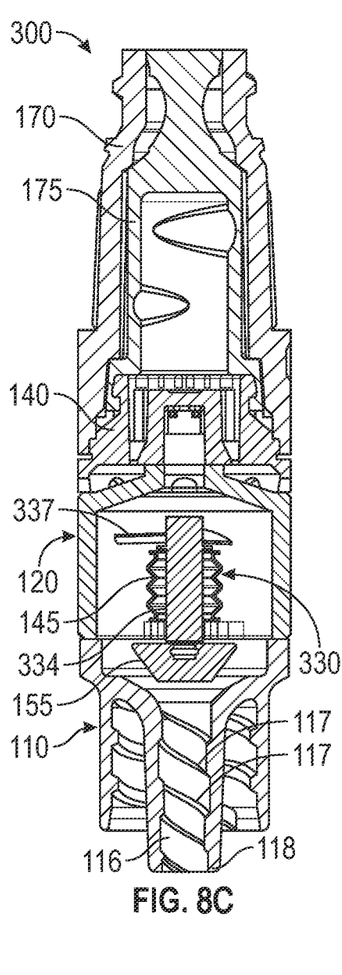
FIG. 8C illustrates a cross-sectional view of the pressure-regulating connector of FIG. 8A, in accordance with some embodiments of the present disclosure.

FIG. 8A illustrates a perspective view of a pressure-regulating connector 300, in accordance with some embodiments of the present disclosure. FIG. 8B illustrates a partially enlarged view of the pressure-regulating connector 300 of FIG. 8A, in accordance with some embodiments of the present disclosure. FIG. 8C illustrates a cross-sectional view of the pressure-regulating connector 300 of FIG. 8A, in accordance with some embodiments of the present disclosure. Similar to the pressure-regulating connector 100, the pressure-regulating connector 300 may include an upper housing 120 including a first internal chamber 126, a lower housing 110 including a second internal chamber 114, a slider 330 disposed and supported at least partially in the first and second internal chambers 126 and 114, and a plug 155 coupled to a distal end of the slider 330. As depicted, the slider 330 may be reciprocally movable between (i) an open position (illustrated in FIGS. 4A and 4B) where the plug 155 at the distal end of the slider 330 is spaced apart from the floor 119 of the second internal chamber 114 to allow the medical fluid to flow through the outlet port, and (ii) a closed position where the plug 155 at the distal end of the slider 330 abuts the floor 119 of the second internal chamber 114 to block the medical fluid from flowing into the fluid channel 115 and through the outlet 118 of the lower housing 110. The slider 330 may be movable to the first or open position when the medical fluid applies a fluid pressure less than or equal to the predetermined threshold, and the slider 330 may be movable to the second position when the medical fluid applies a fluid pressure greater than the predetermined threshold.

In some embodiments, the pressure-regulating connector 300 may include a resilient member 145 mounted in the first internal chamber 126 surrounding at least a portion of the slider 330 to exert a proximal force on the slider 330 such that the resilient member 145 maintains the slider 330 away from the closed position as long as the pressure applied by the medical fluid is lower than or equal to the predetermined threshold. The resilient member 145 may be in the form of a bellows extending around an outer surface of the slider 330. For example, in some embodiments, the resilient member 145 may extend around an outer surface of the stem portion 334 of the slider 330.

As depicted, the slider 330 may include a head portion 332 and a stem portion 334 extending distally from the head portion 132. As depicted, the stem portion 334 may be in the form of an elongate rod connecting the head portion 332 to the plug 155. In some embodiments, the head portion 332 may include a plurality of vanes 337 forming a turbine and extending radially outwards from an outer surface of the elongate rod of stem portion 334. For example, in some embodiments, the plurality of vanes 337 may form a Kaplan turbine. As depicted, the plurality of vanes 337 may be disposed in the first internal chamber 126 at a position proximal to the resilient member 145. The operation of the pressure-regulating connector 300 may be similar to that described with respect to the pressure-regulating connector, except with regards to the head portion 332 as described above. However, in addition, the pressure-regulating connector 300 having the plurality of vanes 337 forming a Kaplan turbine as the head portion 332 may provide the further advantage of inducing additional turbulence of the medical fluid flowing into the lumen 116 of the fluid channel 115 (in addition to the turbulence induced by the threaded profile 117 as discussed above with respect to the pressure-regulating connector 100).

When the medical fluid applies the pressure greater than the predetermined threshold to the head portion 132, a normal component of the force based on the fluid pressure may be transferred to the resilient member 145, causing the resilient member 145 to compress and allow the slider 130 to move distally to the closed position, where the plug 155 blocks the medical fluid from flowing through the outlet 118. Advantageously, a tangential component of the force based on the fluid pressure may induce the additional turbulence in the fluid flow described above.

Figure 9A:
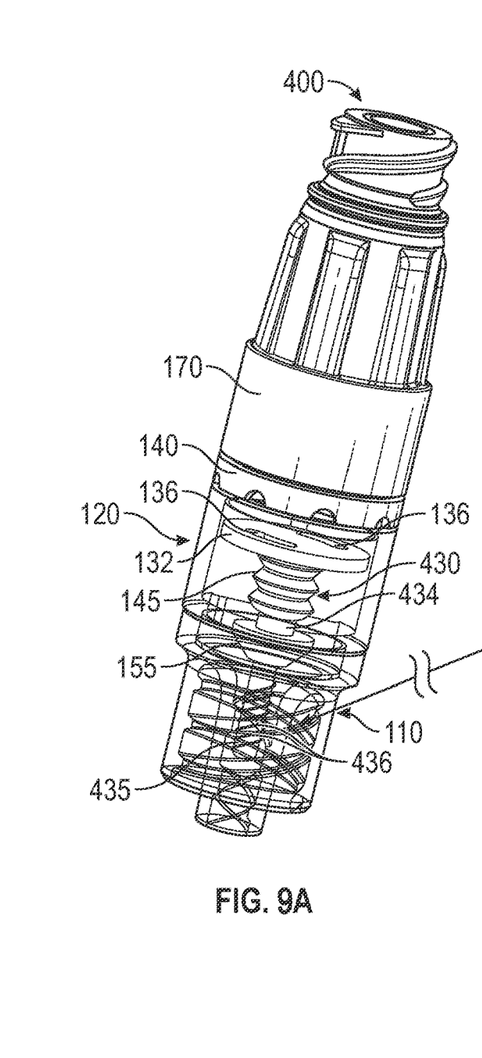
FIG. 9A illustrates a perspective view of a pressure-regulating connector, in accordance with some embodiments of the present disclosure.
Figure 9B:
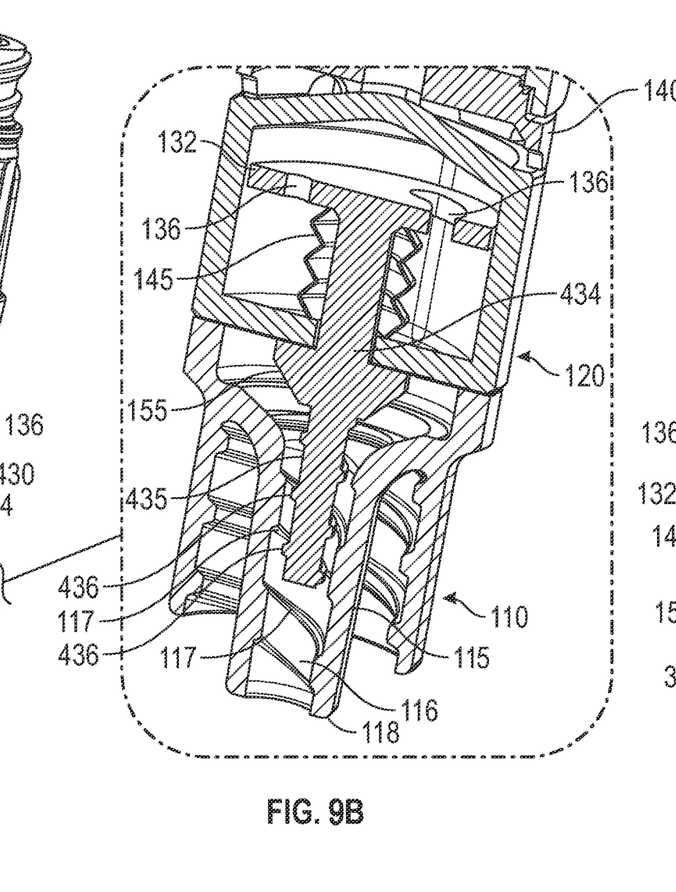
FIG. 9B illustrates a partially enlarged view of the pressure-regulating connector of FIG. 9A, in accordance with some embodiments of the present disclosure.
Figure 9C:
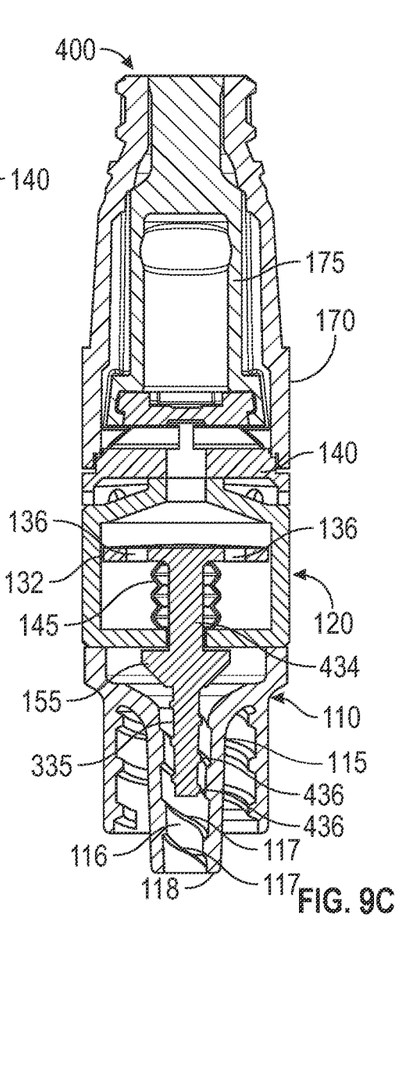
FIG. 9C illustrates a cross-sectional view of the pressure-regulating connector of FIG. 9A, in accordance with some embodiments of the present disclosure.

FIG. 9A illustrates a perspective view of a pressure-regulating connector 400, in accordance with some embodiments of the present disclosure. FIG. 9B illustrates a partially enlarged view of the pressure-regulating connector 400 of FIG. 9A, in accordance with some embodiments of the present disclosure. FIG. 9C illustrates a cross-sectional view of the pressure-regulating connector of FIG. 9A, in accordance with some embodiments of the present disclosure. Similar to the pressure-regulating connector 100, the pressure-regulating connector 400 may include an upper housing 120 including a first internal chamber 126, a lower housing 110 including a second internal chamber 114, a slider 430 disposed and supported at least partially in the first and second internal chambers 126 and 114, and a plug 155 coupled to the slider 230. As depicted, the slider 430 may be reciprocally movable between (i) an open position (illustrated in FIGS. 4A and 4B) where the plug 155 at the distal end of the slider 430 is spaced apart from the floor 119 of the second internal chamber 114 to allow the medical fluid to flow through the outlet port, and (ii) a closed position where the plug at the distal end of the slider 430 abuts the floor 119 of the second internal chamber to block the medical fluid from flowing into the fluid channel 115 and through the outlet 118 of the lower housing 110. The slider 430 may be movable to the first or open position when the medical fluid applies a fluid pressure less than or equal to the predetermined threshold, and the slider 430 may be movable to the second position when the medical fluid applies a fluid pressure greater than the predetermined threshold.

In some embodiments, the pressure-regulating connector 400 may include a resilient member 145 mounted in the first internal chamber 126 surrounding at least a portion of the slider 430 to exert a proximal force on the slider 430 such that the resilient member 145 maintains the slider 430 away from the closed position as long as the pressure applied by the medical fluid is lower than or equal to the predetermined threshold. The resilient member 145 may be in the form of a bellows extending around an outer surface of the slider 430. For example, in some embodiments, the resilient member 145 may extend around an outer surface of the stem portion 434 of the slider 430.

As depicted, the slider 430 may include a head portion 132 and a stem portion 434 extending distally from the head portion 132. When the medical fluid applies the pressure greater than the predetermined threshold to the head portion 132, the resilient member 145 may compress to allow the slider 130 to move distally to the closed position where the plug 155 blocks the medical fluid from flowing through the outlet 118. In some embodiments, the predetermined threshold may be 25 pounds per square inch (psi).

In some embodiments, similar to the pressure-regulating connector 100, the head portion 132 of the slider 430 may have a disc shape. As depicted, the stem portion 434 of the slider 130 may be in the form of an elongate rod connecting the head portion 132 to the plug 155. In some embodiments, the slider 430 may further include an extension member 435 extending longitudinally and distally from the plug 155 into the fluid channel 115. As depicted, the extension member 435 may further include a plurality of threads 436 protruding radially outwards from an outer surface of the extension member 435. For example, in some embodiments, the plurality of threads 436 may be in the form of a plurality of helical threads spaced apart from each other. In other embodiments, the plurality of threads 436 may be in the form of a plurality of circular threads spaced apart from each other.

As depicted, the plurality of threads 436 may be disposed in the lumen 116 of the fluid channel 115. The plurality of threads 436 on the extension member 435 may advantageously guide the fluid entering the lumen 116 and exiting the outlet 118 into a swirling motion, thereby creating turbulence. The operation of the pressure-regulating connector 400 may be similar to that described with respect to the pressure-regulating connector. However, in addition, the pressure-regulating connector 400 having the slider 430 with a plurality of threads 436 disposed in the lumen 116 of the fluid channel 115, may provide the further advantage of inducing additional turbulence of the medical fluid flowing into the fluid channel 115 (in addition to the turbulence induced by the threaded profile 117 of the fluid channel 115, as discussed above with respect to the pressure-regulating connector 100).

The pressure-regulating connectors and systems of the various embodiments described herein additionally provide further advantages over currently existing infusion connectors. For example, pressure-regulating connectors and systems described herein provide a pressure control mechanism integrated with a needleless connector, thereby eliminating the need for additional components, and potentially providing a cost savings. Additionally, the pressure-regulating connectors and systems of the various embodiments described herein may maintain safe infusion pressure by regulating the flow with the reciprocating slider assembly. Furthermore, the pressure-regulating connectors and systems of the various embodiments described herein including the fluid channel with inner surface having threaded profile, which creates turbulent flow, eliminates the need for the push-pause techniques applied by currently existing connectors.

Further advantageously, because the pressure-regulating connectors and systems of the various embodiments incorporate a pressure control mechanisms and pressure selection mechanisms, they advantageously eliminate, or significantly reduce, pain to the patient associated with higher infusion pressures.

Furthermore, the pressure-regulating connectors having the plurality of vanes forming a Kaplan turbine as the head portion may provide the further advantage of inducing additional turbulence of the medical fluid flowing into the lumen of the fluid channel (in addition to the turbulence induced by the threaded profile).

Additionally, the pressure-regulating connector having the plurality of vanes forming a Kaplan turbine on the stem portion may provide the further advantage of inducing additional turbulence of the medical fluid flowing into the lumen of the fluid channel (in addition to the turbulence induced by the threaded profile as discussed above with respect to the pressure-regulating connector).

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A connector for connecting a container containing a medical fluid to a vascular access device, the connector comprising: an upper housing comprising an inlet at a proximal end and an inner surface defining a first internal chamber; a lower housing coupled to the upper housing, and comprising an outlet at a distal end, and an inner surface defining a second internal chamber for circulation of the medical fluid into the outlet; a slider disposed at least partially in the first and second internal chambers; and a plug coupled to a distal end of the slider, wherein the slider is reciprocally movable between (i) an open position, where the plug at the distal end of the slider is spaced apart from a floor of the second internal chamber to allow the medical fluid to flow through the outlet, and (ii) a closed position where the plug at the distal end of the slider abuts the floor of the second internal chamber to block the medical fluid from flowing through the outlet, and wherein the slider is movable to the open position when the medical fluid applies a fluid pressure less than or equal to a predetermined threshold, and the slider is movable to the second position when the medical fluid applies a fluid greater than the predetermined threshold.

Clause 2. The connector of Clause 1, further comprising a resilient member mounted in the first internal chamber surrounding at least a portion of the slider to exert a proximal force on the slider such that the resilient member maintains the slider away from the closed position as long as the pressure applied by the medical fluid is lower than or equal to the predetermined threshold.

Clause 3. The connector of Clause 2, wherein the slider comprises a head portion and a stem portion extending distally from the head portion, and when the medical fluid applies the pressure greater than the predetermined threshold to the head portion, the resilient member compresses to allow the slider to move distally to the closed position where the plug blocks the medical fluid from flowing through the outlet.

Clause 4. The connector of Clause 3, wherein the head portion of the slider comprises a disc shape.

Clause 5. The connector of Clause 3, wherein the head portion of the slider comprises a plurality of vanes forming a turbine and extending radially outward from an outer surface of the stem portion.

Clause 6. The connector of Clause 3, wherein the stem portion of the slider comprises an elongate rod connecting the head portion to the plug.

Clause 7. The connector of Clause 6, wherein the stem portion of the slider comprises a plurality of vanes forming a turbine and extending radially outwards from an outer surface of the elongate rod.

Clause 8. The connector of Clause 7, wherein the plurality of vanes are disposed in the second internal chamber at a position proximal to the plug.

Clause 9. The connector of Clause 3, wherein the head portion of the slider comprises: a peripheral edge configured to guide sliding motion of the slider between the open and closed positions; and at least one aperture extending distally through the head portion, through which the medical fluid flows from the first chamber into the second chamber.

Clause 10. The connector of Clause 9, wherein the at least one aperture comprises a plurality of apertures, the plurality of apertures being symmetrically disposed about a central longitudinal axis of the slider Clause 11. The connector of any one of Clauses 1 to 11, wherein: the lower housing is fluidly communicated with the upper housing via an outlet of the upper housing; and the second internal chamber terminates in a fluid channel extending through the distal end of the lower housing, and a distal end of the fluid channel defines the outlet of the lower housing.

Clause 12. The connector of Clause 11, wherein the fluid channel comprises an inner surface defining a lumen of the fluid channel, and the inner surface has a threaded profile extending at least partially along the inner surface.

Clause 13. The connector of Clause 12, wherein the threaded profile comprises a plurality of helical threads spaced apart from each other.

Clause 14. The connector of Clause 12, wherein the threaded profile comprises a plurality of circular threads spaced apart from each other.

Clause 15. The connector of any one of Clauses 3 to 14, further comprising a needleless connector mounted to the upper housing and fluidly coupled to the slider, wherein the needleless connector comprises a base plate defining an outlet of the needleless connector, and the outlet of the needleless connector and the inlet of the upper housing fluidly communicate a fluid chamber of the needleless connector with the head portion of the slider.

Clause 16. The connector of any one of Clauses 1 to 15, wherein the predetermined threshold is 25 pounds per square inch (psi).

Clause 17. The connector of any one of Clauses 1 to 16, wherein the resilient member comprises a bellows extending around an outer surface of the slider.

Clause 18. A connector for connecting a container containing a medical fluid to a vascular access device, the connector comprising: an upper housing comprising an inlet at a proximal end, an outlet at a distal end, and an inner surface defining a first internal chamber; a lower housing coupled to and fluidly communicated with the upper housing via the outlet, the lower housing comprising a proximal end coupled to the distal end of the upper housing, and defining a second internal chamber extending distally from the proximal end, wherein the second internal chamber terminates in a fluid channel extending through a distal end of the lower housing, and the fluid channel comprises an inner surface having a threaded profile extending at least partially along the inner surface; a slider disposed at least partially in the first and second internal chambers; and a plug coupled to a distal end of the slider, wherein the slider is reciprocally movable between (i) an open position, where the plug at the distal end of the slider is spaced apart from a floor of the second internal chamber to allow the medical fluid to flow through the outlet, and (ii) a closed position where the plug at the distal end of the slider abuts the floor of the second internal chamber to block the medical fluid from flowing into the fluid channel and through the outlet, and wherein the slider is movable to the open position when the medical fluid applies a fluid pressure less than or equal to a predetermined threshold, and the slider is movable to the closed position when the medical fluid applies a fluid pressure greater than the predetermined threshold.

Clause 19. The connector of Clause 18, wherein the threaded profile comprises a plurality of helical threads spaced apart from each other.

Clause 20. The connector of Clause 18, wherein the threaded profile comprises a plurality of circular threads spaced apart from each other.

Clause 21. The connector of Clause 18, further comprising a resilient member mounted in the first internal chamber surrounding at least a portion of the slider to exert a proximal force on the slider such that the resilient member maintains the slider away from the closed position as long as the pressure applied by the medical fluid is lower than or equal to the predetermined threshold.

Clause 22. The connector of Clause 21, wherein the slider comprises a head portion and a stem portion extending distally from the head portion to connect the head portion to the plug, and when the medical fluid applies the pressure greater than the predetermined threshold to the head portion, the resilient member compresses to allow the slider to move distally to the closed position where the plug blocks the medical fluid from flowing through the outlet.

Clause 23. The connector of Clause 22, wherein the head portion of the slider comprises: a peripheral edge configured to guide sliding motion of the slider between the open and closed positions; and at least one aperture extending distally through the head portion, through which the medical fluid flows from the first internal chamber into the second internal chamber.

Clause 24. The connector of Clause 23, wherein the at least one aperture comprises a plurality of apertures, the plurality of apertures being symmetrically disposed about a central longitudinal axis of the slider.

Clause 25. The connector of Clause 22, further comprising a needleless connector mounted to the upper housing and fluidly coupled to the slider, wherein the needleless connector comprises a base plate defining an outlet of the needleless connector, and the outlet of the needleless connector and the inlet of the upper housing fluidly communicate a fluid chamber of the needleless connector with the head portion of the slider.

Clause 26. The connector of any one of Clauses 18 to 25, wherein the predetermined threshold is 25 pounds per square inch (psi).

Clause 27. A connector for connecting a container containing a medical fluid to a vascular access device, the connector comprising: an upper housing comprising an inlet at a proximal end and an inner surface defining a first internal chamber, and a lower housing coupled to the upper housing and comprising an outlet at a distal end and an inner surface defining a second internal chamber terminating in a fluid channel for circulation of the medical fluid into the outlet; a slider disposed at least partially in the first and second internal chambers; a plug coupled to a distal end of the slider; and an extension member extending longitudinally and distally from the plug into the fluid channel, wherein the slider is reciprocally movable between (i) an open position, where the plug at the distal end of the slider is spaced apart from a floor of the second internal chamber to allow the medical fluid to flow through the outlet, and (ii) a closed position where the plug at the distal end of the slider abuts the floor of the second internal chamber to block the medical fluid from flowing through the outlet, and wherein the slider is movable to the open position when the medical fluid applies a fluid pressure less than or equal to a predetermined threshold, and the slider is movable to the second position when the medical fluid applies a fluid pressure greater than the predetermined threshold.

Clause 28. The connector of Clause 27, wherein the extension member comprises a plurality of threads protruding radially outwards from an outer surface of the extension member.

Clause 29. The connector of Clause 28, wherein the plurality of threads comprises a plurality of helical threads spaced apart from each other.

Clause 30. The connector of Clause 28, wherein the plurality of threads comprises a plurality of circular threads spaced apart from each other Clause 31. The connector of Clause 28, further comprising a resilient member mounted in the first internal chamber surrounding at least a portion of the slider to exert a proximal force on the slider such that the resilient member maintains the slider away from the closed position as long as the pressure applied by the medical fluid is lower than or equal to the predetermined threshold.

Clause 32. The connector of any one of Clauses 27 to 31, wherein the slider comprises a head portion and a stem portion extending distally from the head portion, and when the medical fluid applies the pressure greater than the predetermined threshold to the head portion, the resilient member compresses to allow the slider to move distally to the closed position where the plug blocks the medical fluid from flowing through the outlet.

Clause 33. The connector of Clause 32, wherein the head portion of the slider comprises: a peripheral edge configured to guide sliding motion of the slider between the open and closed positions; and at least one aperture extending distally through the head portion, through which the medical fluid flows from the first chamber into the second chamber.

Clause 34. The connector of Clause 33, wherein the at least one aperture comprises a plurality of apertures, the plurality of apertures being symmetrically disposed about a central longitudinal axis of the slider.

Clause 35. The connector of any one of Clauses 27 to 34, wherein the fluid channel comprises an inner surface defining a lumen of the fluid channel, and the inner surface has a threaded profile extending at least partially along the inner surface.

Clause 36. The connector of Clause 35, wherein the threaded profile comprises a plurality of helical threads spaced apart from each other.

Clause 37. The connector of Clause 35, wherein the threaded profile comprises a plurality of circular threads spaced apart from each other.

Clause 38. The connector of any one of Clauses 27 to 37, further comprising a needleless connector mounted to the upper housing and fluidly coupled to the slider, wherein the needleless connector comprises a base plate defining an outlet of the needleless connector, and the outlet of the needleless connector and the inlet of the upper housing fluidly communicate a fluid chamber of the needleless connector with the slider.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A connector for connecting a container containing a medical fluid to a vascular access device, the connector comprising:
   an upper housing comprising an inlet at a proximal end and an inner surface defining a first internal chamber;
   a lower housing coupled to the upper housing, and comprising an outlet at a distal end, and an inner surface defining a second internal chamber for circulation of the medical fluid into the outlet;
   a slider disposed at least partially in the first and second internal chambers, the slider comprising a head portion having at least one aperture extending therethrough such that medical fluid can flow from the first chamber into the second chamber; and
   a plug coupled to the distal end of the slider,
   wherein the slider is reciprocally movable between (i) an open position, where the plug at the distal end of the slider is spaced apart from a floor of the second internal chamber to allow the medical fluid to flow through the outlet, and (ii) a closed position where the plug at the distal end of the slider abuts the floor of the second internal chamber to block the medical fluid from flowing through the outlet, and
   wherein the slider is movable to the open position when the medical fluid applies a fluid pressure less than or equal to a predetermined threshold, and the slider is movable to the closed position when the medical fluid applies a fluid greater than the predetermined threshold.

2. The connector of claim 1, further comprising a resilient member mounted in the first internal chamber surrounding at least a portion of the slider to exert a proximal force on the slider such that the resilient member maintains the slider away from the closed position as long as the pressure applied by the medical fluid is lower than or equal to the predetermined threshold.

3. The connector of claim 2, wherein, when the medical fluid applies the pressure greater than the predetermined threshold to the head portion, the resilient member compresses to allow the slider to move distally to the closed position where the plug blocks the medical fluid from flowing through the outlet.

4. The connector of claim 3, wherein the head portion of the slider comprises a plurality of vanes forming a turbine and extending radially outward from an outer surface of a stem portion of the slider.

5. The connector of claim 3, wherein the head portion of the slider comprises:
   a peripheral edge configured to guide sliding motion of the slider between the open and closed positions.

6. The connector of claim 3, further comprising a needleless connector mounted to the upper housing and fluidly coupled to the slider, wherein the needleless connector comprises a base plate defining an outlet of the needleless connector, and the outlet of the needleless connector and the inlet of the upper housing fluidly communicate a fluid chamber of the needleless connector with the head portion of the slider.

7. The connector of claim 2, wherein the resilient member comprises a bellows extending around an outer surface of the slider.

8. The connector of claim 1, wherein the head portion of the slider comprises a disc shape.

9. The connector of claim 1, wherein the slider comprises a stem portion extending distally from the head portion, the stem portion comprising an elongate rod connecting the head portion to the plug.

10. The connector of claim 9, wherein the stem portion of the slider comprises a plurality of vanes forming a turbine and extending radially outwards from an outer surface of the elongate rod.

11. The connector of claim 10, wherein the plurality of vanes are disposed in the second internal chamber at a position proximal to the plug.

12. The connector of claim 1, wherein:
   the lower housing is fluidly communicated with the upper housing via an outlet of the upper housing; and
   the second internal chamber terminates in a fluid channel extending through the distal end of the lower housing, and a distal end of the fluid channel defines the outlet of the lower housing.

13. The connector of claim 12, wherein the fluid channel comprises an inner surface defining a lumen of the fluid channel, and the inner surface of the fluid channel has a threaded profile extending at least partially along the inner surface of the fluid channel.

14. A connector for connecting a container containing a medical fluid to a vascular access device, the connector comprising:
   an upper housing comprising an inlet at a proximal end and an inner surface defining a first internal chamber, and a lower housing coupled to the upper housing and comprising an outlet at a distal end and an inner surface defining a second internal chamber terminating in a fluid channel for circulation of the medical fluid into the outlet;
   a slider disposed at least partially in the first and second internal chambers, the slider comprising a head portion having at least one aperture extending therethrough such that medical fluid can flow from the first chamber into the second chamber;
   a plug coupled to the distal end of the slider; and
   an extension member extending longitudinally and distally from the plug into the fluid channel,
   wherein the slider is reciprocally movable between (i) an open position, where the plug at the distal end of the slider is spaced apart from a floor of the second internal chamber to allow the medical fluid to flow through the outlet, and (ii) a closed position where the plug at the distal end of the slider abuts the floor of the second internal chamber to block the medical fluid from flowing through the outlet, and wherein the slider is movable to the open position when the medical fluid applies a fluid pressure less than or equal to a predetermined threshold, and the slider is movable to the closed position when the medical fluid applies a fluid pressure greater than the predetermined threshold.

15. The connector of claim 14, wherein the extension member comprises a plurality of threads protruding radially outwards from an outer surface of the extension member.

16. The connector of claim 14, further comprising a resilient member mounted in the first internal chamber surrounding at least a portion of the slider to exert a proximal force on the slider such that the resilient member maintains the slider away from the closed position as long as the pressure applied by the medical fluid is lower than or equal to the predetermined threshold.

17. The connector of claim 16, wherein, when the medical fluid applies the pressure greater than the predetermined threshold to the head portion, the resilient member compresses to allow the slider to move distally to the closed position where the plug blocks the medical fluid from flowing through the outlet.

18. The connector of claim 14, wherein the head portion of the slider comprises:

a peripheral edge configured to guide sliding motion of the slider between the open and closed positions.

19. The connector of claim 14, wherein the fluid channel comprises an inner surface defining a lumen of the fluid channel, and the inner surface of the fluid channel has a threaded profile extending at least partially along the inner surface of the fluid channel.

20. The connector of claim 14, further comprising a needleless connector mounted to the upper housing and fluidly coupled to the slider, wherein the needleless connector comprises a base plate defining an outlet of the needleless connector, and the outlet of the needleless connector and the inlet of the upper housing fluidly communicate a fluid chamber of the needleless connector with the slider.

* * * * *